US010005706B2

United States Patent
Kinage et al.

(10) Patent No.: US 10,005,706 B2
(45) Date of Patent: Jun. 26, 2018

(54) CHIRAL SILICEOUS COMPOSITION USEFUL AS CHIRAL HETEROGENEOUS CATALYST AND A PROCESS FOR THE PREPARATION THEREOF

(71) Applicant: COUNCIL OF SCIENTIFIC & INDUSTRIAL RESEARCH, New Delhi (IN)

(72) Inventors: Anil Kisan Kinage, Pune (IN); Balasaheb Rajendra Javale, Pune (IN); Pralhad Arjun Burate, Pune (IN)

(73) Assignee: COUNCIL OF SCIENTIFIC & INDUSTRIAL RESEARCH, New Delhi (IN)

(*) Notice: Subject to any disclaimer, the term of this patent is extended or adjusted under 35 U.S.C. 154(b) by 0 days. days.

(21) Appl. No.: 15/033,847

(22) PCT Filed: Nov. 3, 2014

(86) PCT No.: PCT/IN2014/000706
§ 371 (c)(1),
(2) Date: May 2, 2016

(87) PCT Pub. No.: WO2015/063800
PCT Pub. Date: May 7, 2015

(65) Prior Publication Data
US 2016/0251287 A1 Sep. 1, 2016

(30) Foreign Application Priority Data

Nov. 1, 2013 (IN) .......................... 3236/DEL/2013
Jun. 20, 2014 (IN) .......................... 1661/DEL/2014

(51) Int. Cl.
| | | |
|---|---|---|
| C07F 7/02 | (2006.01) | |
| C07C 29/143 | (2006.01) | |
| B01J 31/02 | (2006.01) | |
| B01J 29/40 | (2006.01) | |
| B01J 29/50 | (2006.01) | |
| B01J 29/70 | (2006.01) | |
| B01J 29/85 | (2006.01) | |
| B01J 37/00 | (2006.01) | |
| B01J 37/08 | (2006.01) | |
| B01J 37/10 | (2006.01) | |
| C01B 39/40 | (2006.01) | |
| C01B 39/48 | (2006.01) | |
| C01B 39/54 | (2006.01) | |

(52) U.S. Cl.
CPC .......... *C07C 29/143* (2013.01); *B01J 29/40* (2013.01); *B01J 29/50* (2013.01); *B01J 29/7007* (2013.01); *B01J 29/7038* (2013.01); *B01J 29/85* (2013.01); *B01J 31/0274* (2013.01); *B01J 31/0275* (2013.01); *B01J 37/0018* (2013.01); *B01J 37/082* (2013.01); *B01J 37/10* (2013.01); *C01B 39/40* (2013.01); *C01B 39/48* (2013.01); *C01B 39/54* (2013.01); *B01J 2231/643* (2013.01)

(58) Field of Classification Search
CPC ......... C07C 29/143; B01J 29/00; C01B 39/00
USPC ....................................................... 556/173
See application file for complete search history.

(56) References Cited

U.S. PATENT DOCUMENTS

| | | | |
|---|---|---|---|
| 6,713,643 B2 | 3/2004 | Pinnavaia et al. | 556/450 |
| 7,816,435 B2 | 10/2010 | Jiang et al. | 524/263 |
| 8,623,237 B2 | 1/2014 | MacLachlan et al. | 252/299.01 |
| 2004/0267038 A1 | 12/2004 | Tatsumi et al. | 556/413 |
| 2011/0248214 A1 | 10/2011 | Maclachlan et al. | 252/299.01 |

FOREIGN PATENT DOCUMENTS

WO    WO 01/12564    2/2001

OTHER PUBLICATIONS

Ran et al., J. Separation Science, 35(15), 2012, pp. 1854-1862.*
Ran et al., J. Sep. Sci. 2012, 35(15) pp. 1854-1862 (or 1-9 as attached).*
Ran et al., J. Separations Sci. 2012, 35(15), 1854-1862.*
Wang et al. Microporous and Mesoporous Materials 117 (2009) 91-97.*
Ran et al. J. Separations Sci. 2012, 35(15), 1854-1862.*
International Search Report and Written Opinion issued in PCT/IN2014/000706, dated Jul. 20, 2015.
Ran et al., "A novel chiral mesoporous binaphthyl-silicas: Preparation, characterization, and application in HPLC", *J Sep Sci.*, 35: 1854-1862, 2012.
Daschlein et al., "Preparation of "Si-Centered" Chiral Silanes by Direct α-Lithiation of Methylsilanes", *Chem Eur J.*, 16: 4048-4062, 2010.
Che et al., "Synthesis and characterization of chiral mesoporous silica", *Nature*, 429(6989): 281-284, 2004.
Shopsowitz KE et al., "Free-standing mesoporous silica films with tunable chiral nematic structures", Nature, 468(7322):422-425, 2010.
Li-Wen Xu et al., "The recent synthesis and application of silicon-stereogenic silanes: A renewed and significant challenge in asymmetric synthesis", Chem. Soc. Rev., 40: 1777-1790, 2011.
Qihua Yang et al., "Functionalized periodic mesoporous organosilicas for catalysis", J. Mater. Chem., 19: 1945-1955, 2009.

* cited by examiner

*Primary Examiner* — Sudhakar Katakam
*Assistant Examiner* — Kofi Adzamli
(74) *Attorney, Agent, or Firm* — Norton Rose Fulbright US LLP (57) ABSTRACT

The present invention discloses chiral siliceous composition comprising chiral or achiral silane moiety 'A', substituted in another moiety 'B' with tetrahedral metallo-silica or silica framework with mesoporous and microporous structure, useful as chiral heterogeneous catalyst and in enantioselective separations. The invention further discloses a method for introducing molecular level chirality in crystalline framework of silicate and metallosilicate with mesoporous or microporous structure thereof.

14 Claims, 6 Drawing Sheets

CHIRAL SILICEOUS COMPOSITION USEFUL AS CHIRAL HETEROGENEOUS CATALYST AND A PROCESS FOR THE PREPARATION THEREOF

CROSS-REFERENCE TO RELATED APPLICATIONS

This application is a national phase application under 35 U.S.C. § 371 of International Application No. PCT/IN2014/000706 filed 3 Nov. 2014, which claims priority to Indian Patent Application No. 3236/DEL/2013 filed 1 Nov. 2013 and Indian Patent Application No. 1661/DEL/2014 filed 20 Jun. 2014. The entire contents of each of the above-referenced disclosures is specifically incorporated herein by reference without disclaimer.

FIELD OF THE INVENTION

The present invention relates to chiral siliceous composition useful as chiral heterogeneous catalyst and a process for the preparation thereof. Particularly, the present invention provides chiral siliceous composition comprising chiral or achiral silane moiety 'A', substituted in another moiety 'B' with tetrahedral metallo-silica or silica framework with mesoporous or microporous structure, useful as a chiral heterogeneous catalyst. The invention further relates to a method for introducing molecular level chirality in crystalline framework of silicate and metallosilicate with mesoporous or microporous structure thereof.

BACKGROUND AND PRIOR ART

Chirality at the molecular level is found in diverse biological structures, such as polysaccharides, proteins and DNA, and is responsible for many of their unique properties.

Introducing chirality into porous inorganic solids may produce new types of materials that could be useful for chiral separation, stereospecific catalysis, chiral recognition (sensing) and photonic materials. Template (structure directing agent) synthesis of inorganic solids using the self-assembly of lyotropic liquid crystals offers access to materials with well-defined porous structures, but only recently has chirality been introduced into hexagonal porous structures through the use of a chiral surfactant.

The development of a photonic mesoporous inorganic solid that is a cast of a chiral nematic liquid crystal formed from nanocrystalline cellulose is described by Shopsowitz K E et al. in Nature. 2010 Nov. 18; 468(7322):422-5.

U.S. Pat. No. 8,623,237 describes a composition and a method for producing mesoporous silica materials with a chiral organization wherein a polymerizable inorganic monomer is reacted in the presence of nanocrystalline cellulose (NCC) to give a material of inorganic solid with cellulose nanocrystallites embedded in a chiral nematic organization. The NCC can be removed to give a stable porous structure that retains the chiral organization of the NCC template.

U.S. Pat. No. 7,816,435 describes halo-functional silane and process for preparation thereof and, rubber composition containing same and articles manufactured therefrom.

The synthesis and application of silicon-stereogenic silanes by Li-Wen Xu, is disclosed in Chem. Soc. Rev., 2011, 40, 1777-1790. Further the preparation of "Si-centered" chiral silanes by direct α-lithiation of methylsilanes chemistry is reported by Dr. Christian Däschlein in European Journal vol. 16, (13), Pages 4048-4062, Apr. 6, 2010.

Recently Shunai Che et al. in Nature 429, 281-284 (20 May 2004) has reported templating route for preparing well-ordered mesoporous silicas based on the self-assembly of chiral anionic surfactants and inorganic precursors by using aminosilane or quaternized aminosilane as a co-structure-directing agent (CSDA), which is provided a potential method to synthesize mesoporous materials with inherent chirality.

WO0112564 relates to crystalline inorganic-organic oxide composition which are functionalized using organo silane and to the process of synthesis thereof. The process comprises reacting an inorganic oxide precursor and a hydrolyzable organic silane in the presence of water and a structure directing template having a hydrophobic and hydrophilic moiety to provide the composition.

US20040267038 relates to a mesoporous silica utilizing the structure of a self-assembled anionic surfactant as the template, characterized by using a basic silane, and a process for producing the same. The organo alkoxy silane with quaternary ammonium organic group (N-trimethoxylsilyl-propyl-N,N,N-tributylammounium) has been used as the structure directing agent of zeolites ZSM-5 and ZSM-11. The hydrothermal process disclosed in US '038 comprises reacting an organo silane, a silicon precursor and anionic surfactant and washing with an acidic aqueous solution, a water-miscible organic solvent, or an aqueous solution or calcination to remove the anionic surfactant.

Functionalization of mesoporous silicas by incorporating heteroatoms either in the pore wall or on the pore surface or by anchoring organic groups onto their surface to create active sites for catalysis, selective adsorption, and separation is disclosed in article titled 'Functionalized periodic mesoporous organosilicas for catalysis' by Qihua Yang et al. in J. Mater. Chem., 2009, 19, 1945-1955.

U.S. Pat. No. 6,713,643 relates to mesostructured and microporous to mesoporous organo functionalized silica compositions. The compositions incorporate the organo functional group L as part of $LSiO_3$ unit in the framework of the compositions. In addition the compositions incorporate the organo functional group R as part of $O_3Si$—R—$SiO_3$ unit in the framework of the compositions. The compositions are useful as molecular sieves, supports for catalysts and numerous other applications requiring an organo group on surfaces of silica.

With a view that, introducing molecular level chirality in to the silica framework can give rise to enormous possibilities for tuning the characters of chiral composition which can widen its scope in industrial applications, the present inventors felt a need to provide novel chiral composition by introduction of molecular level chirality into silica framework of crystalline mesoporous or microporous material.

OBJECTS OF THE INVENTION

The main object of the present invention is to provide chiral siliceous composition useful as chiral heterogeneous catalyst and a process for the preparation thereof.

Another object of the present invention is to provide chiral siliceous moiety comprising chiral or achiral silane moiety substituted in another moiety with tetrahedral metallo-silica or silica framework with mesoporous or microporous structure useful as an asymmetric heterogeneous catalyst and material useful in enantioselective separations.

Yet another object of the present invention is to provide a novel process for the synthesis of said composition thereof.

SUMMARY OF THE INVENTION

Accordingly, the present invention provides a chiral siliceous composition comprising;
achiral or chiral silane moiety of formula 'A';

Formula A wherein $R_1$ and $R_2$, are independently selected from the group consisting of (un)substituted or substituted branched or linear ($C_1$-$C_6$) alkyl, (un)substituted or substituted branched or linear ($C_1$-$C_4$) alkenyl, (un)substituted or substituted aryl, (un)substituted or substituted aralkyl, or halogen, alkoxy or —OH;
R3 or R4 are hydrogen or halogen; and
wherein achiral crystalline tetrahedral framework 'B' selected from the group consisting of molecular sieves, zeolites, zeolite like material, silicates, metallo-silicates, silica alumina phosphates, and silica metallophosphates with porosity in the range of 0.1 nm to 50 nm;
wherein the achiral or chiral silane moiety of formula 'A' is substituted at positions Q1, Q2, Q3 and Q4 in to the crystalline tetrahedral framework 'B';

In one embodiment of the present invention, the chiral or achiral silane of formula A is selected from the group consisting of dichloropropyl methyl silane and trichlorosilane.

In an embodiment of the present invention said chiral siliceous composition optionally comprises chiral amino acid selected from Alanine or Proline along with achiral silane of formula A in 1:1 molar ratio.

In another embodiment of the present invention said chiral siliceous composition comprises 3.1Na$_2$O:1Al$_2$O$_3$:25SiO$_2$:5 chiral silane.

The present invention provides a process for preparation of chiral siliceous composition, comprising the steps of:
a. hydrothermal crystallizing chiral silane moiety from a gel (pH 8-13) consisting of silica precursor, sodium-precursor and/or metal salts, organic template at temperature in the range of 150 to 195° C. for a period in the range of 24 to 240 hr to obtain metallosilicate crystals or silicate crystals having chiral silica moiety inside the framework;
b. drying the crystals of step (a) followed by removing the organic template by calcining at temperature in the range of 500 to 600° C. for a period in the range of 12 to 15 hr to obtain the calcined metallo-silicates;
c. optionally refluxing crystals of step (a) with 30-40% HCl in methanol followed by drying to obtain the organic template free metallo-silicates;
d. subjecting the calcined metallo-silicates of step (b) to ion exchange process with NH$_4$NO$_3$ solution and repeating the ion exchange process to obtain the NH$_4$-metallosilicates or silicates; and
e. calcining NH$_4$-metallosilicates of step (d) at temperature in the range of 500 to 600° C. for a period in the range of 12 to 15 hr to obtain chiral siliceous material.

Yet in another embodiment of the present invention chiral siliceous material of step (e) is in H-form.

Still in another embodiment of the present invention chiral silane of step (a) is prepared by mixing achiral silane (A) and chiral amino acids (Alanine or L-Proline) in 1:1 mole ratio and refluxing the mixture to obtain solid chiral silane.

Still in another embodiment of the present invention the achiral or chiral silane moiety comprises the compound of formula 'A';

Formula A wherein R1 and R2, are independently selected from the group consisting of (un)substituted or substituted branched or linear (C1-C6) alkyl, (un)substituted or substituted branched or linear (C1-C4) alkenyl, (un)substituted or substituted aryl, (un)substituted or substituted aralkyl, or halogen, alkoxy or —OH; and
R3 or R4 are hydrogen or halogen;
wherein achiral crystalline tetrahedral framework 'B' selected from the group consisting of molecular sieves, zeolites, zeolite like material, silicates, metallo-silicates, silica alumina phosphates, and silica metallophosphates with porosity in the range of 0.1 nm to 50 nm;
wherein the achiral or chiral silane moiety of formula 'A' is substituted at positions Q1, Q2, Q3 and Q4 in to the crystalline tetrahedral framework 'B';

prepared by the process comprising the steps of:
a. hydrothermal crystallizing chiral silane moiety from a gel (pH 8-13) consisting of silica precursor, sodium-precursor and/or metal salts, organic template at temperature in the range of 150 to 195° C. for a period in the range of 24 to 240 hr to obtain metallosilicate crystals or silicate crystals having chiral silica moiety inside the framework;
b. drying the crystals of step (a) followed by removing the organic template by calcining at temperature in the range of 500 to 600° C. for a period in the range of 12 to 15 hr to obtain the calcined metallo-silicates;

c. optionally refluxing crystals of step (a) with 30-40% HCl in methanol followed by drying to obtain the organic template free metallo-silicates;

d. subjecting the calcined metallo-silicates of step (b) to ion exchange process with $NH_4NO_3$ solution and repeating the ion exchange process to obtain the $NH_4$-metallosilicates or silicates; and e. calcining $NH_4$-metallosilicates of step (d) at temperature in the range of 500 to 600° C. for a period in the range of 12 to 15 hr to obtain chiral siliceous material in their H-form.

In another embodiment of the present invention the chiral silane of step (a) comprises achiral silane moiety of formula 'A' and chiral amino acid in 1:1 molar ratio.

Yet another embodiment of the present invention the organic template is selected from the group consisting of 1,2,3 triblock copolymer, tetrapropyl ammonium hydroxide, cyclohexylamine, tetraalkyl ammonium hydroxide, tetraalkyl ammonium halides, cetyltrimethylammonium bromide, and hexamethylamine.

Still in another embodiment of the present invention silica precursor is selected from the group consisting of tetraethylorthosilicate (TEOS), ethyl silicate fumed silica, water glass, sodium silicate, and sodium trisilicates.

In another embodiment of the present invention sodium precursor is selected from the group consisting of sodium aluminate, sodium isopropoxide, and sodium hydroxide.

Still in another embodiment of the present invention metal salt is selected from the group consisting of KNO3, NaNO3, pseudoboehmite AlO(OH), ferric nitrate, galium nitrate, tin nitrate, and titanium isopropoxide.

Yet another embodiment of the present invention provides chiral siliceous composition for use as heterogeneous recyclable catalyst in asymmetric transformations selected from the group consisting of asymmetric Aldol reaction, asymmetric Michael reaction, Asymmetric C—C and C—N bond formation, asymmetric transfer hydrogenation of C=O, N=O, C=C and hydrogenation using molecular hydrogen and other asymmetric transformation reactions.

In another embodiment of the present invention provides chiral siliceous composition with achiral silane moiety 'A' and chiral amino acid in 1:1 molar ratio substituted in to the crystalline moiety with tetrahedral metallo-silica or silica framework 'B' for use as heterogeneous recyclable catalyst in asymmetric transformations selected from the group consisting of asymmetric Aldol reaction, asymmetric Michael reaction, Asymmetric C—C and C—N bond formation, asymmetric transfer hydrogenation of C=O, N=O, C=C and hydrogenation using molecular hydrogen and other asymmetric transformation reactions.

DETAILED DESCRIPTION OF THE INVENTION

Figure 1:
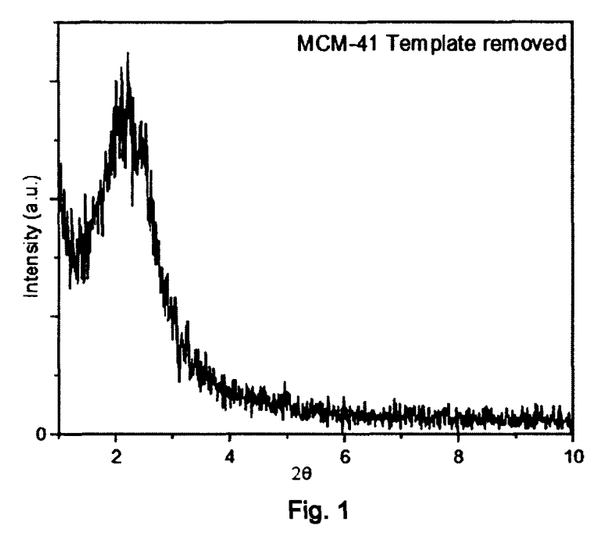
FIG. 1: XRD data of MCM-41 structure type mesoporous material.

The present invention provides chiral siliceous composition comprising achiral or chiral silane moiety of Formula 'A';

Formula A wherein $R_1$ and $R_2$, are independently selected from the group consisting of (un)substituted or substituted branched or linear ($C_1$-$C_6$) alkyl, (un)substituted or substituted branched or linear ($C_1$-$C_4$) alkenyl, (un)substituted or substituted aryl, (un)substituted or substituted aralkyl, or halogen, alkoxy or —OH;

R3 or R4 are hydrogen or halogen; and wherein achiral crystalline tetrahedral framework 'B' selected from the group consisting of molecular sieves, zeolites, zeolite like material, silicates, metallo-silicates, silica alumina phosphates, and silica metallo-phosphates with porosity in the range of 0.1 nm to 50 nm;

wherein the achiral or chiral silane moiety of Formula 'A' is substituted at positions Q1, Q2, Q3 and Q4 in to the crystalline tetrahedral framework 'B' as shown in FIG. 1 below;

FIG. 1

In an aspect, the present invention optionally provides chiral silane moiety comprising achiral silane moiety 'A' and chiral amino acid in 1:1 molar ratio substituted in to the crystalline tetrahedral framework 'B' selected from molecular sieves, zeolites, zeolite like material, silicates, metallosilicates, silica alumina phosphates, silica metallo-phosphates with porosity in the range of 0.1 nm to 50 nm.

Figure 2:
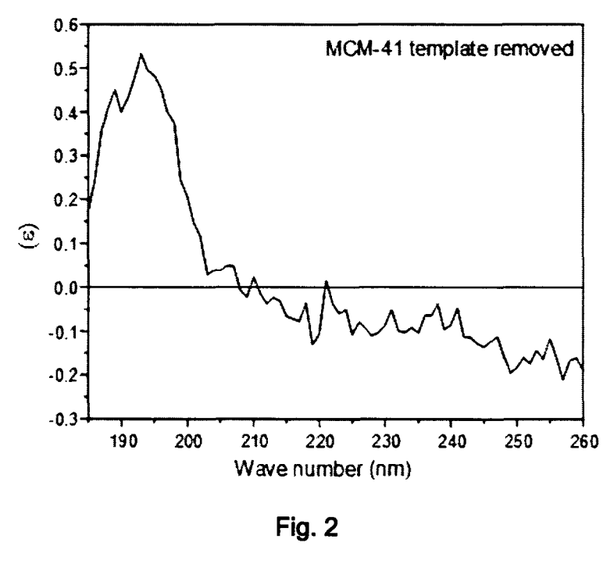
FIG. 2: Circular dichroism spectra of mesoporous material taken after removal of organic structure directing agent. This confirms that the material has Chirality.
Figure 3:
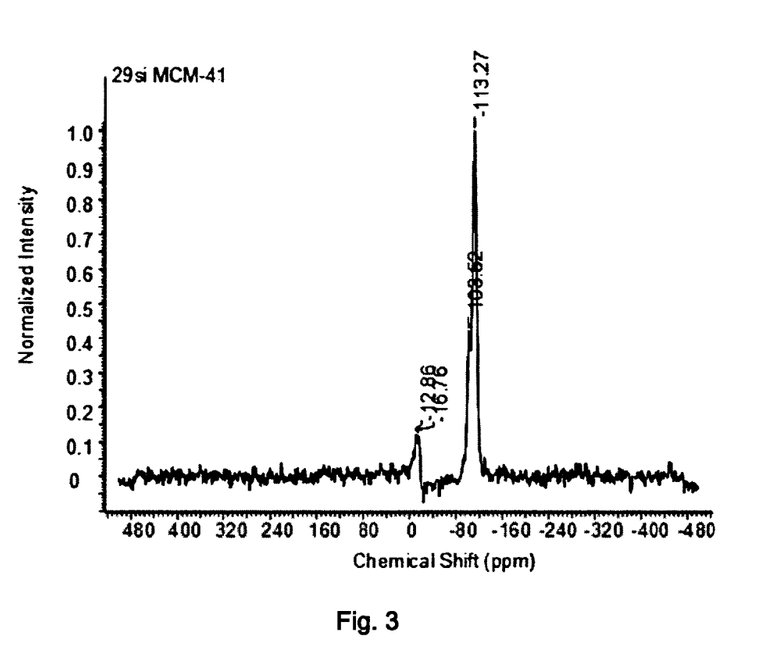
FIG. 3: $^{29}Si$ solid state MAS NMR confirms the species at 12.8, 16.8, 100 and 113 are $Q_1$, $Q_2$, $Q_3$ and $Q_4$.
Figure 4:
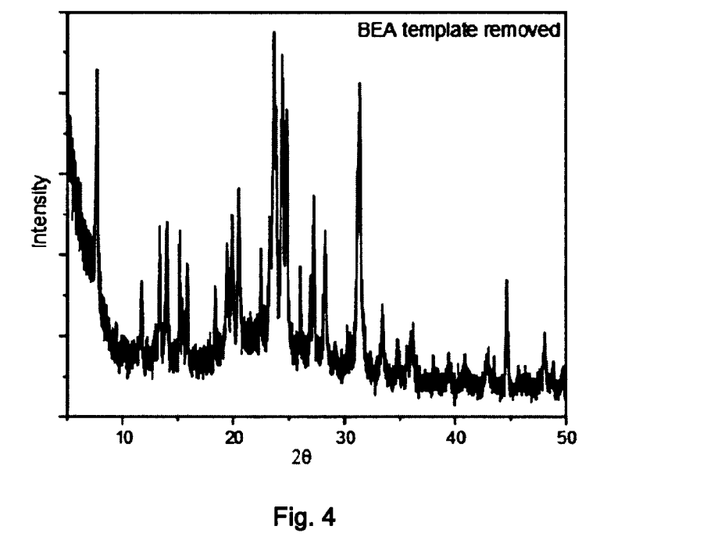
FIG. 4: XRD data confirms the BEA type structure.
Figure 5:
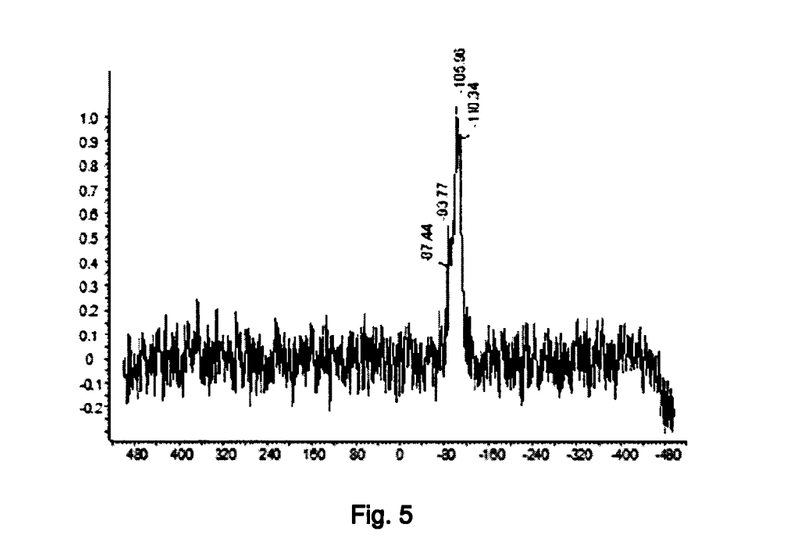
FIG. 5: $^{29}Si$ solid state MAS NMR confirms the species at −87.44, −93.77, 105.96 and −110.34 are $Q_1$, $Q_2$, $Q_3$ and $Q_4$.
Figure 6:
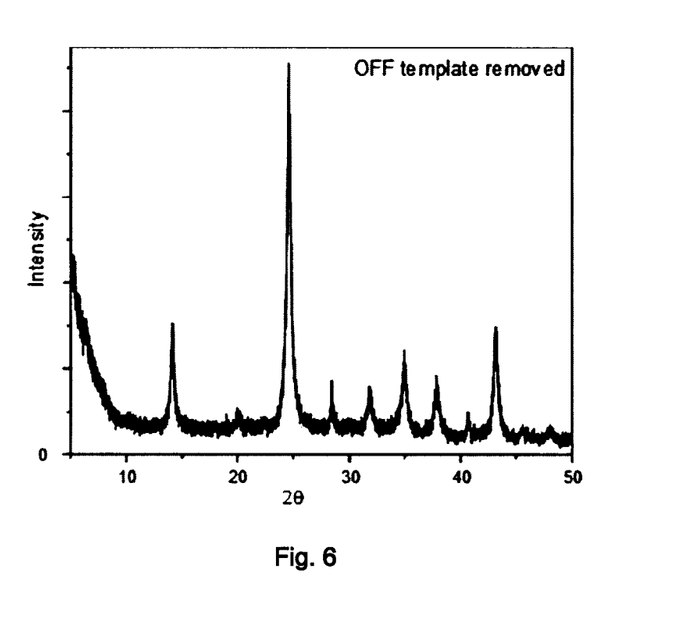
FIG. 6: XRD data confirms OFF structure.
Figure 7:
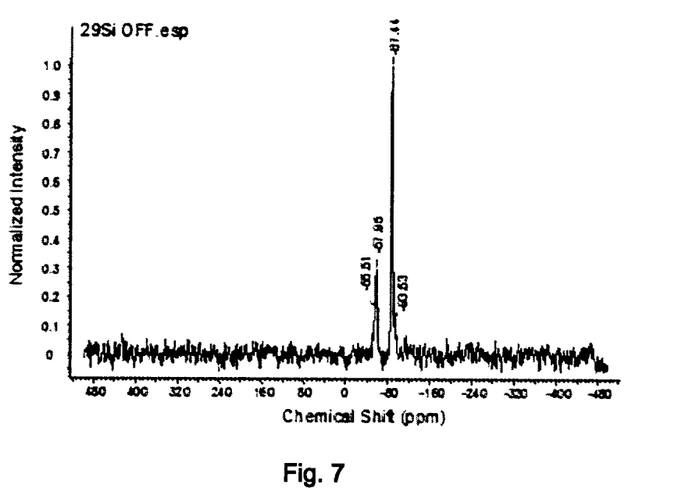
FIG. 7: $^{29}Si$ solid state MAS NMR confirms the species at −55.51, −57.95, −87.44 and 93.53 are $Q_1$, $Q_2$, $Q_3$ and $Q_4$.
Figure 8:
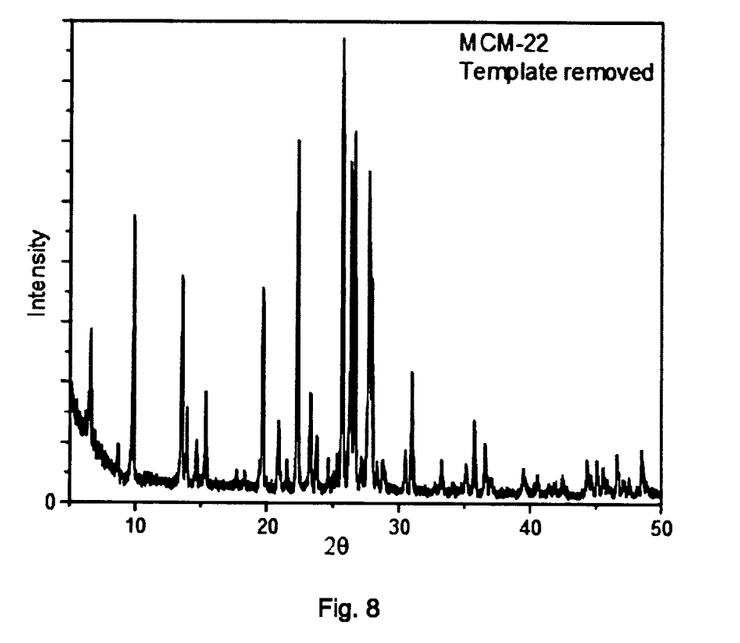
FIG. 8: XRD data confirms MCM-22 type structure.
Figure 9:
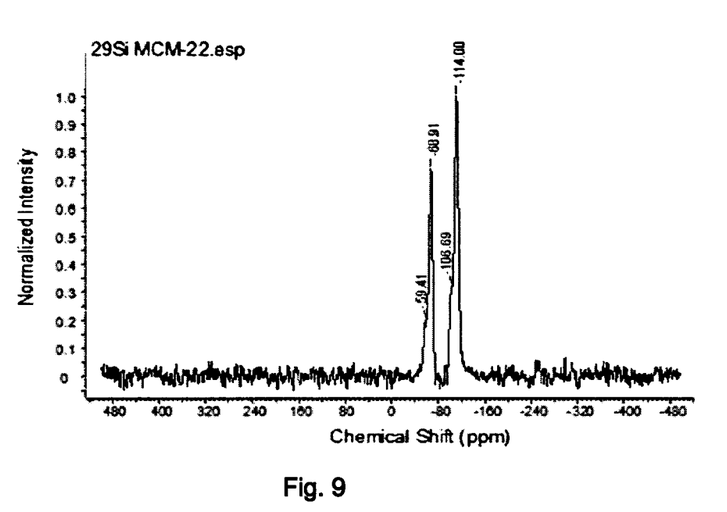
FIG. 9: $^{29}Si$ solid state MAS NMR confirms the species at −59.41, −68.91, 106.69 and −114.00 are $Q_1$, $Q_2$, $Q_3$ and $Q_4$.
Figure 10:
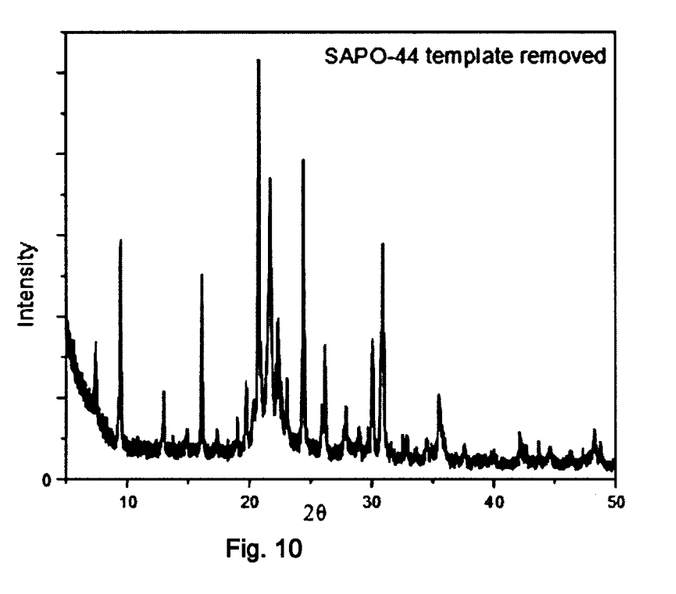
FIG. 10: XRD data confirms SAPO-44 structure.
Figure 11:
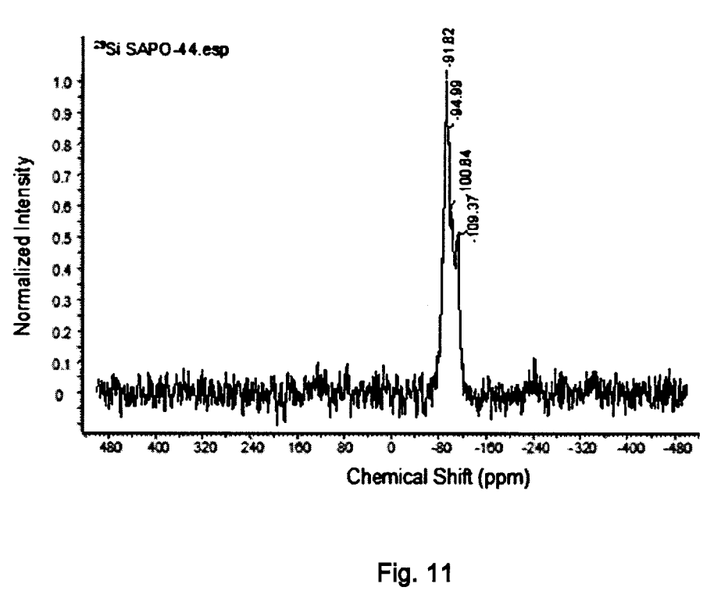
FIG. 11: $^{29}Si$ solid state MAS NMR confirms the species at −91.82, 84.99, 100.84 and −109.37 are $Q_1$, $Q_2$, $Q_3$ and $Q_4$.

The mesoporous or microporous chiral siliceous composition of the present invention comprises a framework as depicted in FIGS. 2 and 3 below, wherein in the achiral or chiral silane moiety of Formula 'A' is substituted at positions Q1, 'B' one silicon atom is attached to through oxygen to the crystalline tetrahedral framework and other three bond are formed by three different molecules as shown in Fig below;

FIG. 2

FIG. 3

In another aspect, the achiral or chiral silane moiety of formula 'A' of the present invention comprises;

dichloropropyl methyl silane

Trichlorosilane

The present invention provides a process for preparation of chiral siliceous composition comprising;
a) hydrothermal crystallizing chiral silane moiety from a gel (pH 8-13) consisting of Na-precursor and/or metal salts silica precursor, organic template and water with molar gel composition $3.1Na_2O:1Al_2O_3:25SiO_2:5$ achiral Silane:0.5 organic template:950 $H_2O$ in a stainless steel autoclave with or without Teflon lining at suitable crystallization temperature and time to afford the metallosilicate crystals or silicate crystals having chiral silica moiety inside the framework;
b) drying the crystals of step (a) followed by removing the organic template by calcining in static or flowing air to obtain the calcined metallo-silicates or optionally refluxing crystals of step (b) with 30-40% HCl in methanol followed by drying to obtain the calcined metallo-silicates;
c) subjecting the organic template free metallo-silicates or silicates of step (b) to ion exchange process with $NH_4NO_3$ solution and repeating the ion exchange process to obtain the $NH_4$-metallosilicates or silicates; and
d) calcining $NH_4$-metallosilicates of step (c) to afford the desired metallo-silicates or silicates in their H-form.

In an aspect, the pore size of the siliceous composition of the present invention depends on structure directing agent used to construct the crystalline tetrahedral silica framework.

In yet another aspect, the present invention provides a chiral siliceous composition having the formula $3.1Na_2O:1Al_2O_3:25SiO_2:5$ chiral Silane when written in template/surfactant free, dehydroxylated and anhydrous form, where fraction of the framework silicon centers that have been functionalized.

The chiral or achiral silane moiety 'A' used in the process comprises;

Formula A wherein R1 and R2, are independently selected from the group consisting of (un)substituted or substituted branched or linear (C1-C6) alkyl, (un)substituted or substituted branched or linear (C1-C4) alkenyl, (un)substituted or substituted aryl, (un)substituted or substituted aralkyl, or halogen, alkoxy or —OH; and
R3 or R4 are hydrogen or halogen;
optionally, the chiral silane moiety used in the process comprises achiral silane moiety 'A' and chiral amino acid (Alanine or L-Proline) in 1:1 molar ratio.

The organic template used in the process is also referred as 'organic structure directing agent' and is selected from the group consisting of 1,2,3 triblock copolymer, tetrapropyl ammonium hydroxide, cyclohexylamine, tetraalkyl ammonium hydroxide, tetralkyl ammonium halides, cetyltrimethylammonium bromide, and hexamethylamine.

The silica precursor employed in the process is selected from the group consisting of tetraethylorthosilicate (TEOS), ethyl silicate fumed silica, water glass, sodium silicate, and sodium trisilicates; the Na-precursor is selected from the group consisting of sodium aluminate, sodium isopropoxide, and sodium hydroxide.

The metal salt is selected from the group consisting of nitre or $KNO_3$, $NaNO_3$, pseudoboehmite AlO(OH), ferric nitrate, galium nitrate, tin nitrate, and titanium isopropoxide.

The base employed in the process is selected from the group consisting of alkali or alkaline metal hydroxides, preferable alkali metal hydroxide such as NaOH or KOH, whereas the acid is selected from hydrochloric acid or orthophosphoric acid.

According to the process, to the mixture containing silica precursor, chiral silane (A) and base is added an organic template or the surfactant dissolved in DI water and stirred for about 2-3 hours. The pH of the gel formed was kept in the range of 8-13. The gel is then transferred in stainless steel autoclave (with or without Teflon lining) and for crystallization the autoclave is heated at a temperature in the range of 80° C. to 200° C. in oven for 1 to 8 days to afford the desired metallosilicate crystals or silicate crystals having chiral silica moiety inside the framework.

After crystallization the white colored powder is filtered and washed with deionized water and dried at a temperature in the range of 100-150° C. for 10-20 hrs. In said process the organic template is removed either by transferring the crystals into-round-bottomed flask equipped with a magnetic stirring and reflux condenser containing mixture of acidic alcohol followed by refluxing for 10-15 hrs or optionally by calcining white powder at elevated temperature for about 500-600° C. in furnace at static or under flowing gas.

The mixture of acidic alcohol comprises concentrated inorganic acid in lower alcohol i.e. (C1-C4) alkyl alcohol, such as HCl in methanol, HBr in methanol, HF in methanol, HI in methanol, HCl in propanol, HI in propanol; preferably acidic alcohol is 30-40% HCl in methanol.

For creating acid sites useful in catalytic reaction, the organic template free metallo-silicates or silicates is subjected to ion exchange which is carried out in presence of salt such as $NH_4NO_3$, $KNO_3$, ammonium acetate solution and repeating the ion exchange process for 4-8 times to obtain the cation saturated metallo silicates; preferably ion exchange is carried out with $NH_4NO_3$ solution and repeating the ion exchange process for about five times to obtain the $NH_4$-metallosilicates, which is further calcined by means of static or flowing air to obtain desired metallo-silicates or silicates in their H-form. The H-form of the material is having acidic site which is catalytic active site for acid catalyzed reactions.

In yet another embodiment, the instant chiral siliceous composition is characterized by means of XRD, FTIR, 1H-NMR, $^{13}$C-NMR, 29Si MAS NMR, UV spectroscopy, spectro-polarimeter.

The optical rotation of the instant chiral siliceous composition is evaluated in the range of −0.005° to −0.5°, wherein specific optical rotation $[\alpha]_D$ is present in the range of −900° to −1200°.

The other distinguishing feature of the compositions described is the exceptional degree of framework crossing achieved in the assembly process. The silane substituted in framework generates the chiral silica in structural framework of material at position of Q1 Q2, Q3 or Q4.

The present invention relates to a process for the synthesis of a composition comprising:
a. mixing silane (A) and chiral amino acids (Alanine or L-Proline) in 1:1 mole ratio and refluxing the mixture to obtain solid chiral silane;
b. hydrothermal crystallization of chiral silane of step (a) from a gel (pH 8-13) consisting of silica precursor, Na-precursor or metal salts, organic template (as structure directing agents), in a stainless steel autoclave with or without Teflon lining at desired crystallization temperature and for desired crystallization time affords the metallosilicate crystals;
c. drying the crystals of step (b) and removing the organic template by calcining in static or flowing air to obtain the calcined metallo-silicates or optionally refluxing crystals of step (b) with 30-40% HCl in methanol followed by drying to obtain the calcined metallo-silicates;
e) subjecting the organic template free metallo-silicates or silicates of step (b) to ion exchange process with $NH_4NO_3$ solution and repeating the ion exchange process to obtain the $NH_4$-metallosilicates or silicates; and
f) calcining $NH_4$-metallosilicates of step (c) to afford the desired metallo-silicates or silicates in their H-form.

The present invention relates to chiral siliceous composition having the formula $3.1Na_2O:1\ Al_2O_3:25SiO_2:5$ chiral silane when written in template/surfactant free, dehydroxylated and anhydrous form, where fraction of the framework silicon centres that have been functionalized.

The present invention discloses a chiral siliceous composition comprising chiral or achiral silane moiety of Formula 'A' substituted in to the crystalline moiety with tetrahedral metallo-silica or silica framework wherein the said composition can be used as an asymmetric heterogeneous catalyst and in enantioselective separations.

The present invention discloses a chiral siliceous composition comprising chiral or achiral silane moiety of Formula 'A' substituted in to the crystalline moiety with tetrahedral metallo-silica or silica framework 'B' wherein the said composition can be used as heterogeneous recyclable catalyst in asymmetric transformations such as asymmetric Aldol reaction, asymmetric Michael reaction, Asymmetric C—C and C—N bond formation, asymmetric transfer hydrogenation of C=O, N=O, C=C and hydrogenation using molecular hydrogen and other asymmetric transformation reactions.

The present invention discloses chiral siliceous composition comprising achiral silane moiety of Formula 'A' and chiral amino acid in 1:1 molar ratio substituted in to the crystalline moiety with tetrahedral metallo-silica or silica framework 'B' wherein said composition can be used as heterogeneous recyclable catalyst in asymmetric transformations such as asymmetric Aldol reaction, asymmetric Michael reaction, Asymmetric C—C and C—N bond formation, asymmetric transfer hydrogenation of C=O, N=O, C=C and hydrogenation using molecular hydrogen and other asymmetric transformation reactions.

The present invention disclose heterogeneous recyclable catalyst in asymmetric transformations wherein asymmetric transformations can be carried out in batch mode and continuous flow operational mode and/or gas-solid phase as well as in liquid-solid phase in various reactors.

The present invention relates to chiral siliceous composition comprising chiral or achiral silane moiety of Formula 'A' substituted in to the crystalline moiety with tetrahedral metallo-silica or silica framework wherein said composition can be used in asymmetric/enantioselective separations.

The present invention relates to chiral siliceous composition comprising achiral silane moiety of Formula 'A' and chiral amino acid in 1:1 ratio substituted in to the crystalline moiety with tetrahedral metallo-silica or silica framework wherein said composition can be used in asymmetric/enantioselective separations.

The invention relates to use of instant chiral siliceous composition as heterogeneous recyclable catalyst, particularly use of synthesized Small-Pore Molecular Sieves (SAPO-44) as catalyst in asymmetric hydrogenation of acetophenone in presence of organic solvent such as methanol, ethanol, isopropanol and like thereof to give phenyl ethanol with more than 80% yield and more than 80% enantioselectivity (ee) as depicted herein below scheme 1.

EXAMPLES

The following examples are given by way of illustration of the working of the invention in actual practice and should not be construed to limit the scope of the present invention in any way.

Example 1

1) Synthesis of Mesoporous Material Having Chiral Silica in the Tetrahedral Framework In typical synthesis procedure, 8 gm of 1,2,3 triblock copolymer [poly(ethylene glycol)-block-poly(propylene glycol)-block-poly(ethylene glycol)] (as structure directing agent or surfactant) with 60 ml deionized water is taken in beaker and vigorously stirred until the polymer is completely dissolved. In this 240 ml 2N HCl was added drop by drop using burette under stirring. Then 15.2 gm tetraethylorthosilicate (TEOS) was added drop by drop under stirring followed by addition of 2.7 gm dichloropropyl methyl silane. The above gel was stirred for 24 h. The pH of gel was 3-4. After 24 h the gel was aged in oven at 100° C. for 24 h. The white colour powder formed was filtered and washed with deionised water and dried in oven at 120° C. for 15 hr. Further the organic template was removed either by transferring into round-bottomed flask equipped with a magnetic stirring and reflux condenser containing mixture of 30% hydrochloric acid (HCl) in methanol and refluxed for 12 hr at 60° C. or by calcining white powder at 550° C. for 12 hr in furnace. The white powder then was ion exchanged with 1 molar solution of ammonium acetate or ammonium nitrate. The ion exchange was performed 5 times to get NH4 form of the material, which was further calcined at 550° C. to obtain H-form for the material which has acidity sites useable for acid catalysed reactions.

1.1 Characterization

The above white colour powder was characterized after removal of organic template. To confirm the structure, XRD (using Phillips diffractometer 1730 series with CuKα as source of radiation) and FTIR (using Agilent Technologies carry 600 series) in activated KBr pallets) was used and $^1$H, and $^{13}$C NMR (using Bruker MSL 400 MHz NMR instrument) confirms the organic molecules attached to chiral silica and $^{29}$Si MAS NMR spectra (Bruker NMR MSL300 MHz NMR, 2 μsec pulse, a flip angle of 458, and samples spun at 3-3.5 kHz) confirms the Q1, Q2, Q3, and Q4, species in tetrahedral framework of silica. The Chirality was confirmed by circular dichroism spectrometer (by far UV CD spectrum measured on J-720W spectro-polarimeter (JASCO) with 10 mm path length quartz cell,ab8 8 s time constant, a 20 nm/min scan speed and 9 time accumulation) and by measuring optical rotation using polarimeter (JASCO POLARIMETER at room temperature with 1 mg/ml sample concentration in water). The optical rotation observed was −0.0073 and specific rotation observed was −1009.6 which confirms the chiral moiety in molecule.

2)

In typical synthesis procedure, 9.9 gm of 1:1 refluxed mixture of achiral silica and alanine or proline [tetrahedral chiral silica (TCS)] was added in mixture of 15.5 gm tetraethylorthosilicate (TEOS) and 1.5 gm of sodium hydroxide (NaOH). The mixture was stirred for 1 h and denoted as mixture 'A'. In mixture 'A' 5 gm of cetyltrimethylammonium bromide (CTMA-Br) as structure directing agent (template) and 75 ml deionised water was added and stirred for another 2 hr. The pH of the gel formed was kept at pH 9. The gel was then transferred in stainless steel autoclave (with or without Teflon lining) and for crystallization the autoclave was heated at 110° C. in oven for 3 days. The white colour powder formed was filtered and washed with deionised water and dried in oven at 120° C. for 15 hr. Further the organic template was removed either by transferring into round-bottomed flask equipped with a magnetic stirring and reflux condenser containing mixture of 30% hydrochloric acid (HCl) in methanol and refluxed for 12 hr at 60° C. or by calcining white powder at 550° C. for 12 hr in furnace. The white powder then was ion exchanged with 1 molar solution of ammonium acetate or ammonium nitrate. The ion exchange was perform 5 times to get NH4 form of the material, which was further calcined at 550° C. for 12 hr to obtain H-form for the material which has acidity sites useable for acid catalysed reactions.

1.1 Characterization

The above white colour powder was characterized after removal of organic template. To confirm the structure, XRD (using Phillips diffractometer 1730 series with CuKα as source of radiation) and FTIR (using Agilent Technologies carry 600 series) in activated KBr pallets) was used and $^1$H, and $^{13}$C NMR (using Bruker MSL 400 MHz NMR instrument) confirms the organic molecules attached to chiral silica and $^{29}$Si MAS NMR spectra (Bruker NMR MSL300 MHz NMR, 2 μsec pulse, a flip angle of 458, and samples spun at 3-3.5 kHz) confirms the $Q_1$, $Q_2$, $Q_3$, and $Q_4$, species in tetrahedral framework of silica. The Chirality was confirmed by circular dichroism spectrometer (by far UV CD spectrum measured on J-720W spectro-polarimeter (JASCO) with 10 mm path length quartz cell,ab8 8 s time constant, a 20 nm/min scan speed and 9 time accumulation) and by measuring optical rotation using polarimeter (JASCO POLARIMETER at room temperature With 1 mg/ml sample concentration in water). The optical rotation observed is −0.802° and specific rotation observed is −1.7626° confirms the chiral moiety in molecule.

Example 2

2) Synthesis of Zeolite Type or Zeolite Like Material Having BETA or MCM-22 or OFF Type Structure Having Chiral Silica in the Tetrahedral Framework

A. Synthesis of Zeolite Beta Type or Like Structure:

In typical synthesis procedure, to 59.5 gm of deionised water taken in polypropylene beaker was added 89.5 gm tetraethyl ammonium hydroxide (TEOH) as structure directing agent (template) drop wise with constant stirring. The addition was completed in 30 min followed by adding 0.5 gm sodium chloride and 1.5 gm potassium chloride and stirred the solution for further 30 min until complete dissolution denoted as mixture 'A', to the mixture 'A', 32.5 gm of tetraethylorthosilicate (TEOS) was added drop by drop and stirred until homogeneous mixture was formed. This was followed by addition of 11.5 gm of 1:1 refluxed mixture of achiral silica and alanine or proline [tetrahedral chiral silica (TCS)] and stirred until complete dissolution. The mixture is denoted as B. Further, 0.4 gm sodium hydroxide (NaOH) dissolved in 20 ml deionised water and 1.8 gm sodium aluminate was added drop by drop in solution B under stirring till gel formation. The gel was stirred for 2 hr. The pH of the gel formed was maintained at pH 12. The gel was then transferred in stainless steel autoclave (with or without Teflon lining) and for crystallization the autoclave was heated at 170° C. in oven for 9 days. The white colour powder formed was filtered and washed with deionised water and dried in oven at 120° C. for 15 hr. Further the organic template was removed either by transferring into round-bottomed flask equipped with a magnetic stirring and reflux condenser containing mixture of 30% hydrochloric acid (HCl) in methanol and refluxed for 12 hr at 60° C. or by calcining white powder at 550° C. for 12 hr in furnace. The white powder then was ion exchanged with 1 molar solution of ammonium acetate or ammonium nitrate. The ion exchange was perform 5 times to get NH4 form of the material, which further calcined at 550° C. for 12 hr to obtain H-form for the material which has acidity sites useable for acid catalysed reactions.

2.1 Characterization

The above white colour powder was characterized after removal of organic template. To confirm the structure, XRD (using Phillips diffractometer 1730 series with CuKα as source of radiation) and FTIR (using Agilent Technologies carry 600 series) in activated KBr pallets) was used and $^1$H, and $^{13}$C NMR (using Bruker MSL 400 MHz NMR instrument) confirms the organic molecules attached to chiral silica and $^{29}$Si MAS NMR spectra (Bruker NMR MSL300 MHz NMR, 2 μsec pulse, a flip angle of 458, and samples spun at 3-3.5 kHz) confirms the Q1, Q2, Q3, and Q4, species in tetrahedral framework of silica. The Chirality was confirmed by circular dichroism spectrometer (by far UV CD spectrum measured on J-720W spectro-polarimeter (JASCO) with 10 mm path length quartz cell,ab8 8 s time constant, a 20 nm/min scan speed and 9 time accumulation) and by measuring optical rotation using polarimeter (JASCO POLARIMETER at room temperature with 1 mg/ml sample concentration in water). The optical rotation observed was 0.1207° and specific rotation observed at −2.1563° confirming the chiral moiety in molecule.

B. Synthesis of Zeolite OFF Type or Like Structure

In typical synthesis procedure, 10 gm of deionised water was taken in polypropylene beaker. 4.6 gm of NaOH and 3.5 g of KOH was added to the beaker and stirred the solution until complete dissolution. The mixture was denoted as mixture 'A'. In mixture 'A', 6.5 gm of tetraethylorthosilicate (TEOS) was added drop by drop and stirred until homogeneous mixture of slightly yellow colour appeared. This was followed by addition of 4.1 gm of 1:1 refluxed mixture of achiral silica and alanine or proline [tetrahedral chiral silica (TCS)] was added in mixture and stirred until it was com-pletely dissolved and mixture was denoted as solution 'B'. Further, 7.7 gm of sodium aluminate was added in solution B under stirring till gel formation. The gel was stirred for 3 hr. The pH of the gel formed was maintained at pH 12. The gel was then transferred in stainless steel autoclave (with or without Teflon lining) and for crystallization the autoclave was heated at 150° C. in oven for 8 days. The white colour powder formed was filtered and washed with deionised water and dried in oven at 120° C. for 15 hr. The white powder then was ion exchanged with 1 molar solution of ammonium acetate or ammonium nitrate. The ion exchange was perform 5 times to get NH4 form of the material, which further calcined at 550° C. for 15 hr to obtain H-form for the material which has acidity sites useable for acid catalysed reactions.

2.2 Characterization

The above white colour powder was characterized after removal of organic template. To confirm the structure, XRD (using Phillips diffractometer 1730 series with CuKα as source of radiation) and FTIR (using Agilent Technologies carry 600 series) in activated KBr pallets) was used and $^1$H, and $^{13}$C NMR (using Bruker MSL 400 MHz NMR instrument) confirms the organic molecules attached to chiral silica and $^{29}$Si MAS NMR spectra (Bruker NMR MSL300 MHz NMR, 2 μsec pulse, a flip angle of 458, and samples spun at 3-3.5 kHz) confirms the Q1, Q2, Q3, and Q4, species in tetrahedral framework of silica. The Chirality was confirmed by circular dichroism spectrometer (by far UV CD spectrum measured on J-720W spectro-polarimeter (JASCO) with 10 mm path length quartz cell,ab8 8 s time constant, a 20 nm/min scan speed and 9 time accumulation) and by measuring optical rotation using polarimeter (JASCO POLARIMETER at room temperature with 1 mg/ml sample concentration in water). The optical rotation observed was −0.1033° and specific rotation observed is −2.0664° confirms the chiral moiety in molecule.

C. Synthesis of Zeolite MCM-22 Type or Like Structure:

In typical synthesis procedure, 70 gm of deionised water was taken in polypropylene beaker, to that 1 gm sodium aluminate and 0.5 gm sodium hydroxide was added and stirred for 30 min. to dissolve. The mixture was denoted as mixture 'A'. In mixture 'A', 8.5 ml hexamethylimine (as structure directing agent (template) was added and stirred for 1 hr. Further 26 gm of tetraethylorthosilicate (TEOS) was added drop by drop and stirred until homogeneous mixture was obtained. This was followed by adding 5.5 gm of 1:1 refluxed mixture of achiral silica and alanine or proline [tetrahedral chiral silica (TCS)] was added under stirring till gel formation. The gel was stirred for 2 hr. The pH of the gel formed was maintained at pH 12. The gel was then transferred in stainless steel autoclave (with or without Teflon lining) and for crystallization the autoclave was heated at 170° C. in oven for 10 days. The white colour powder formed was filtered and washed with deionised water and dried in oven at 120° C. for 15 hr. Further the organic template was removed either by transferring into round-bottomed flask equipped with a magnetic stirring and reflux condenser containing mixture of 30% hydrochloric acid (HCl) in methanol and refluxed for 12 hr at 55° C. or by calcining white powder at 550° C. for 15 hr in furnace. The white powder then was ion exchanged with 1 molar solution of ammonium acetate or ammonium nitrate. The ion exchange was perform 5 times to get NH4 form of the material, which further calcined at 550° C. for 15 hr to obtain H-form for the material which has acidity sites useable for acid catalysed reactions.

2.3 Characterization

The above white colour powder was characterized after removal of organic template. To confirm the structure, XRD (using Phillips diffractometer 1730 series with CuKα as source of radiation) and FTIR (using Agilent Technologies carry 600 series) in activated KBr pallets) was used and $^1H$, and $^{13}C$ NMR (using Bruker MSL 400 MHz NMR instrument) confirms the organic molecules attached to chiral silica and $^{29}Si$ MAS NMR spectra (Bruker NMR MSL300 MHz NMR, 2 μsec pulse, a flip angle of 458, and samples spun at 3-3.5 kHz) confirms the Q1, Q2, Q3, and Q4, species in tetrahedral framework of silica. The Chirality was confirmed by circular dichroism spectrometer (by far UV CD spectrum measured on J-720W spectro-polarimeter (JASCO) with 10 mm path length quartz cell,ab8 8 s time constant, a 20 nm/min scan speed and 9 time accumulation) and by measuring optical rotation using polarimeter (JASCO POLARIMETER at room temperature with 1 mg/ml sample concentration in water). The optical rotation observed is −0.1523° and specific rotation observed is −2.2361° confirms the chiral moiety in molecule.

Example 3

3) Synthesis of Molecular Sieves Silica-Metallo-Phosphate Having Chiral Silica in the Tetrahedral Framework A. Synthesis of Molecular Sieve Silica Aluminophosphate Having SAPO-34 Type or Like Structure:

In typical synthesis procedure, 45 gm of deionised water was taken in polypropylene beaker, in that 17 gm orthophosphoric was added and stirred for 30 min. 1:1 refuxed mixture of achiral silica and alanine or proline to this 11 gm of pseudoboehmite was added and stirred until gel forms, which is denoted as mixture 'A'. To the mixture A, 30 gm cyclohexylamine as structure directing agent (template) was added and stirred for 1 hr. Further, 12 gm of tetraethylorthosilicate (TEOS) was added drop by drop and stirred until homogeneous mixture was obtained. This was followed by addition of 3.5 gm of 1:1 refuxed mixture of achiral silica and alanine or proline [tetrahedral chiral silica (TCS)] was added under stirring till gel formation. The gel was stirred for 2 hr. The pH of the gel formed was maintained at a pH in the range 6-7. The gel was then transferred in stainless steel autoclave (with or without Teflon lining) and for crystallization the autoclave was heated at 190° C. in oven for 5 days. The white colour powder formed was filtered and washed with deionised water and dried in oven at 120° C. for 15 hr. Further the organic template was removed either by transferring into round-bottomed flask equipped with a magnetic stirring and reflux condenser containing mixture of 30% hydrochloric acid (HCl) in methanol and refluxed for 12 hr at 55° C. or by calcining white powder at 550° C. for 15 hr in furnace. The white powder then was ion exchanged with 1 molar solution of ammonium acetate or ammonium nitrate. The ion exchange was perform 5 times to get NH4 form of the material, which further calcined at 550° C. for 15 hr to obtain H-form for the material which has acidity sites useable for acid catalysed reactions.

3.1 Characterization

The above white colour powder was characterized after removal of organic template. To confirm the structure, XRD (using Phillips diffractometer 1730 series with CuKα as source of radiation) and FTIR (using Agilent Technologies carry 600 series) in activated KBr pallets) was used and $^1H$, and $^{13}C$ NMR (using Bruker MSL 400 MHz NMR instrument) confirms the organic molecules attached to chiral silica and $^{29}Si$ MAS NMR spectra (Bruker NMR MSL300 MHz NMR, 2 μsec pulse, a flip angle of 458, and samples spun at 3-3.5 kHz) confirms the Q1, Q2, Q3, and Q4, species in tetrahedral framework of silica. The Chirality was confirmed by circular dichroism spectrometer (by far UV CD spectrum measured on J-720W spectro-polarimeter (JASCO) with 10 mm path length quartz cell,ab8 8 s time constant, a 20 nm/min scan speed and 9 time accumulation) and by measuring optical rotation using polarimeter (JASCO POLARIMETER at room temperature with 1 mg/ml sample concentration in water). The optical rotation observed is 0.3619° and specific rotation observed is 7.2372° confirms the chiral moiety in molecule.

Example 3

Synthesis of Zeolite Type or Zeolite Like Material Having ZSM-5 Type Structure with Chiral Silica in the Tetrahedral Framework D. Synthesis of Zeolite ZSM-5 Type or Like Structure In typical synthesis procedure, 86 gm of deionised water was taken in polypropylene beaker, in that 1.3 gm of NaOH and 1 gm of sodium aluminate was added and stirred the solution for 30 min. To this mixture 5 gm of tetrapropyl ammonium hydroxide was added drop by drop and mixture was stirred for 30 min followed by addition of 26 gm of tetraethylorthosilicate (TEOS) and 4 gm of dichloromethyl propyl silane. The mixture was further stirred for another 1 h. The pH of the gel formed was maintained at pH 12. The gel was then transferred in stainless steel autoclave (with or without Teflon lining) and for crystallization the autoclave was heated at 150° C. in oven for 7 days. The white colour powder formed was filtered and washed with deionised water and dried in oven at 120° C. for 15 hr. Further the organic template was removed either by transferring into round-bottomed flask equipped with a magnetic stirring and reflux condenser containing mixture of 30% hydrochloric acid (HCl) in methanol and refluxed for 12 hrs 55 to 60° C. or by calcining white powder at 550° C., 12 to 15 hr in furnace. The white powder then was ion exchanged with 1 molar solution of ammonium acetate or ammonium nitrate. The ion exchange was perform 5 times to get NH4 form of the material, which further calcined at 550° C. 12 to 15 hr to obtain H-form for the material which has acidity sites useable for acid catalysed reactions.

2.4 Characterization

The above white colour powder was characterized after removal of organic template. To confirm the structure, XRD (using Phillips diffractometer 1730 series with CuKα as source of radiation) and FTIR (using Agilent Technologies carry 600 series) in activated KBr pallets) was used and $^1H$, and $^{13}C$ NMR (using Bruker MSL 400 MHz NMR instrument) confirms the organic molecules attached to chiral silica and $^{29}Si$ MAS NMR spectra (Bruker NMR MSL300 MHz NMR, 2 μsec pulse, a flip angle of 458, and samples spun at 3-3.5 kHz) confirms the Q1, Q2, Q3, and Q4, species in tetrahedral framework of silica. The Chirality was confirmed by circular dichroism spectrometer (by far UV CD spectrum measured on J-720W spectro-polarimeter (JASCO) with 10 mm path length quartz cell,ab8 8 s time constant, a 20 nm/min scan speed and 9 time accumulation) and by measuring optical rotation using polarimeter (JASCO POLARIMETER at room temperature With 1 mg/ml sample concentration in water). The optical rotation observed is −0.0133° and specific rotation observed is −968.3° confirms the chiral moiety in molecule.

Example 3: Synthesis of Molecular Sieves Silica-Metallo-Phosphate Having Chiral Silica in the Tetrahedral Framework (A) Synthesis of Molecular Sieve Silica Aluminophosphate Having SAPO-44 Type or Like Structure:

In typical synthesis procedure, 45 gm of deionised water was taken in polypropylene beaker, in that 17 gm orthophosphoric was added and stirred for 30 min. To this 11 gm of pseudoboehmite was added and stirred until gel formation and is denoted as mixture 'A'. To the mixture 'A', 14 gm cyclohexylamine as structure directing agent (template) was added and stirred for 1 hr. Further, 12 gm of tetraethylorthosilicate (TEOS) was added drop by drop and stirred until homogeneous mixture was formed. Further 2.8 gm of dichloropropyl methyl silane was added under stirring till gel formation. The gel was stirred for 2 hr. The pH of the gel formed was maintained 6-7. The gel was then transferred in stainless steel autoclave (with or without Teflon lining) and for crystallization the autoclave was heated at 190° C. in oven for 5 days. The white colour powder formed was filtered and washed with deionised water and dried in oven at 120° C. for 15 hr. Further the organic template was removed either by transferring into round-bottomed flask equipped with a magnetic stirring and reflux condenser containing mixture of 30% hydrochloric acid (HCl) in methanol and refluxed for 12 hr at 60° C. or by calcining white powder at 550° C. for 12 hr in furnace. The white powder then was ion exchanged with 1 molar solution of ammonium acetate or ammonium nitrate. The ion exchange was perform 5 times to get NH4 form of the material, which further calcined at 550° C. for 15 hr to obtain H-form for the material which has acidity sites useable for acid catalysed reactions.

3.1 Characterization

The above white colour powder was characterized after removal of organic template. To confirm the structure, XRD (using Phillips diffractometer 1730 series with CuKα as source of radiation) and FTIR (using Agilent Technologies carry 600 series) in activated KBr pallets) was used and $^1$H, and $^{13}$C NMR (using Bruker MSL 400 MHz NMR instrument) confirms the organic molecules attached to chiral silica and $^{29}$Si MAS NMR spectra (Bruker NMR MSL300 MHz NMR, 2 μsec pulse, a flip angle of 458, and samples spun at 3-3.5 kHz) confirms the Q1, Q2, Q3, and Q4, species in tetrahedral framework of silica. The Chirality was confirmed by circular dichroism spectrometer (by far UV CD spectrum measured on J-720W spectro-polarimeter (JASCO) with 10 mm path length quartz cell,ab8 8 s time constant, a 20 nm/min scan speed and 9 time accumulation) and by measuring optical rotation using polarimeter (JASCO POLARIMETER at room temperature With 1 mg/ml sample concentration in water). The optical rotation observed is −0.2814° and specific rotation observed is −950.1° confirms the chiral moiety in molecule.

Example 4

Asymmetric Transfer Hydrogenation of Acetophenone by Using the Chiral Composition of Example 3A Having SAPO-44 Type Structure

Catalytic reaction was carried out using a 100-mL round-bottomed flask equipped with a magnetic stirring and reflux condenser charged with 50 mmol of acetophenone, 75 ml isopropyl alcohol and 25 mg of above synthesized catalyst of example 3A. The mixture was vigorously stirred and refluxed at ~80° C. for 15 h. Thus product obtained was isolated and analyzed by NMR and optical rotation. The Phenyl ethanol was obtained with 82% yield and 83% enantioselectivity (ee).

Advantages of the Invention a. The invention provides chiral siliceous composition comprising achiral silane of formula 'A' substituted in the crystalline framework with tetrahedral metallo-silica or silica framework with better porosity, surface area 450 m$^2$/g.
b. A non-catalytic route to synthesis of chiral alkylsilanes.
c. Acts as chiral heterogeneous catalyst in asymmetric aldol condensation reaction, asymmetric transfer hydrogenation and hydrogenation using molecular hydrogen and other asymmetric type reactions.
d. The catalyst is applicable for both batch and continuous processes and is recyclable.
e. Composition can be used in asymmetric/enantioselective separations.

We claim:

1. A chiral siliceous composition comprising:

wherein:
crystalline tetrahedral framework 'B' is selected from the group consisting of molecular sieves, zeolites, zeolite like material, metallo-silicates, silica alumina phosphates, and silica metallo-phosphates with porosity in the range of 0.1 nm to 50 nm; and
chiral silane moiety of formula 'A' is substituted at positions Q1, Q2, Q3 and Q4 into the crystalline tetrahedral framework 'B':

wherein $R_1$, $R_2$, $R_3$ and $R_4$ are independently selected from the group consisting of hydrogen, (un)substituted or substituted branched or linear ($C_1$-$C_6$) alkyl, (un)substituted or substituted branched or linear ($C_1$-$C_4$) alkenyl, (un)substituted or substituted aryl, (un)substituted or substituted aralkyl, halogen, alkoxy or —OH, and chiral amino acids selected from alanine or proline.

2. The chiral siliceous composition of claim 1, wherein said composition comprises 3.1Na$_2$O:1Al$_2$O$_3$:25SiO$_2$:5 chiral silane.

3. The chiral siliceous composition of claim 2, wherein the chiral or achiral silane is selected from the group consisting of dichloropropyl methyl silane and trichlorosilane along with amino acid selected from alanine or Proline 1:1 molar ratio.

4. A process for preparation of a chiral siliceous composition of claim 2, comprising the steps of:
  (a) hydrothermal crystallizing chiral silane moiety from a gel (pH 8-13) consisting of silica precursor, sodium precursor and/or metal salt, organic template at temperature in the range of 150 to 195° C. for a period in the range of 24 to 240 hr to obtain metallosilicate crystals or silicate crystals having chiral silica moiety inside the framework;
  (b) drying the crystals of step (a) followed by removing the organic template by calcining at temperature in the range of 500 to 600° C. for a period in the range of 12 to 15 hr to obtain the calcined metallo-silicates;
  (c) subjecting the calcined metallo-silicates of step (b) to ion exchange process with $NH_4NO_3$ solution and repeating the ion exchange process to obtain the $NH_4$-metallosilicates or silicates; and
  (d) calcining $NH_4$-metallosilicates of step (c) at temperature in the range of 500 to 600° C. for a period in the range of 12 to 15 hr to obtain chiral siliceous material.

5. The process of claim 4, wherein chiral siliceous material of step (d) is in H-form.

6. The process of claim 4, further comprising refluxing crystals of step (a) with 30-40% HCl in methanol followed by drying to obtain the organic template free metallo-silicates.

7. The process of claim 4, wherein chiral silane (A) of step (a) is prepared by mixing achiral silane and chiral amino acids (Alanine or L-Proline) in 1:1 mole ratio and refluxing the mixture to obtain solid chiral silane.

8. The process of claim 4, wherein the chiral silane moiety of formula 'A'

A wherein R1, R2, R3 and R4 are independently selected from the group consisting of hydrogen, (un)substituted or substituted branched or linear ($C_1$-$C_6$) alkyl, (un)substituted or substituted branched or linear ($C_1$-$C_4$) alkenyl, (un)substituted or substituted aryl, (un)substituted or substituted aralkyl, halogen, alkoxy or —OH; and chiral amino acids selected from alanine or proline; and wherein achiral crystalline tetrahedral framework 'B' selected from the group consisting of molecular sieves, zeolites, zeolite like material, metallo-silicates, silica alumina phosphates, and silica metallo-phosphates with porosity in the range of 0.1 nm to 50 nm;

wherein the chiral silane moiety of formula 'A' is substituted at positions Q1, Q2, Q3 and Q4 in to the crystalline tetrahedral framework 'B'

9. The process of claim 4, wherein the organic template is selected from the group consisting of 1,2,3 triblock copolymer, tetrapropyl ammonium hydroxide, cyclohexylamine, tetraalkyl ammonium hydroxide, tetralkyl ammonium halides, cetyltrimethylammonium bromide, and hexamethylamine.

10. The process of claim 4, wherein silica precursor is selected from the group consisting of tetraethylorthosilicate (TEOS), ethyl silicate fumed silica, water glass, sodium silicate, and sodium trisilicates.

11. The process of claim 4, wherein sodium precursor is selected from the group consisting of sodium aluminate, sodium isopropoxide, and sodium hydroxide.

12. The process of claim 4, wherein metal salt is selected from the group consisting of KNO3, NaNO3, pseudoboehmite AlO(OH), ferric nitrate, galium nitrate, tin nitrate, and titanium isopropoxide.

13. A process comprising:
  obtaining a chiral siliceous composition of claim 1; and
  using the chiral siliceous composition as a heterogeneous recyclable catalyst in an asymmetric transformation reaction.

14. The process of claim 13, wherein the asymmetric transformation reaction is further defined as an asymmetric Aldol reaction, an asymmetric Michael reaction, an asymmetric C—C or C—N bond formation, or an asymmetric transfer hydrogenation of C=O, N=O, C=C, or hydrogenation using molecular hydrogen.

* * * * *